United States Patent
Maurer et al.

(10) Patent No.: US 11,918,011 B2
(45) Date of Patent: Mar. 5, 2024

(54) HIGH-PAYLOAD, NON-POROUS, ENZYME-CONTAINING COATED GRANULES AND USE OF SAME

(71) Applicant: DANISCO US INC, Palo Alto, CA (US)

(72) Inventors: Samuel A. Maurer, Palo Alto, CA (US); Nathaniel T. Becker, Palo Alto, CA (US); Douglas A. Dale, Palo Alto, CA (US); Peyman Moslemy, Palo Alto, CA (US); Michael Reichman, Palo Alto, CA (US); Alan Martin Allgeier, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 635 days.

(21) Appl. No.: 15/734,065

(22) PCT Filed: May 30, 2019

(86) PCT No.: PCT/US2019/034503
§ 371 (c)(1),
(2) Date: Dec. 1, 2020

(87) PCT Pub. No.: WO2019/232119
PCT Pub. Date: Dec. 5, 2019

(65) Prior Publication Data
US 2021/0219574 A1    Jul. 22, 2021

Related U.S. Application Data

(60) Provisional application No. 62/679,415, filed on Jun. 1, 2018.

(51) Int. Cl.
| | | |
|---|---|---|
| *A23K 20/189* | (2016.01) | |
| *A23K 20/22* | (2016.01) | |
| *A23K 40/10* | (2016.01) | |
| *A23K 40/30* | (2016.01) | |
| *C12N 9/16* | (2006.01) | |
| *C12N 9/96* | (2006.01) | |

(52) U.S. Cl.
CPC ............ *A23K 20/189* (2016.05); *A23K 20/22* (2016.05); *A23K 40/10* (2016.05); *A23K 40/30* (2016.05); *C12N 9/16* (2013.01); *C12N 9/96* (2013.01); *C12Y 301/03* (2013.01)

(58) Field of Classification Search
CPC .... A23K 20/22; A23K 20/189; C12Y 301/03; C12N 9/16; C12N 9/96
See application file for complete search history.

(56) References Cited

U.S. PATENT DOCUMENTS

| | | | | |
|---|---|---|---|---|
| 8,734,849 B2 * | 5/2014 | Lizio | .................. | A61P 5/18 424/490 |
| 2010/0004170 A1 * | 1/2010 | Winter | .................. | A23P 20/10 424/94.1 |
| 2018/0092379 A1 * | 4/2018 | Becker | .................. | A23K 40/30 |

FOREIGN PATENT DOCUMENTS

| | | | |
|---|---|---|---|
| KR | 2014010803 | * | 1/2014 |
| WO | WO2014205161 | * | 12/2014 |
| WO | WO2016149636 | * | 9/2016 |

* cited by examiner

*Primary Examiner* — Anthony J Weier

(57) ABSTRACT

Described are compositions and methods relate to stable, high-payload, non-porous enzyme-containing coated granules with improved resistance to activity loss during steam pelleting.

50 Claims, 1 Drawing Sheet

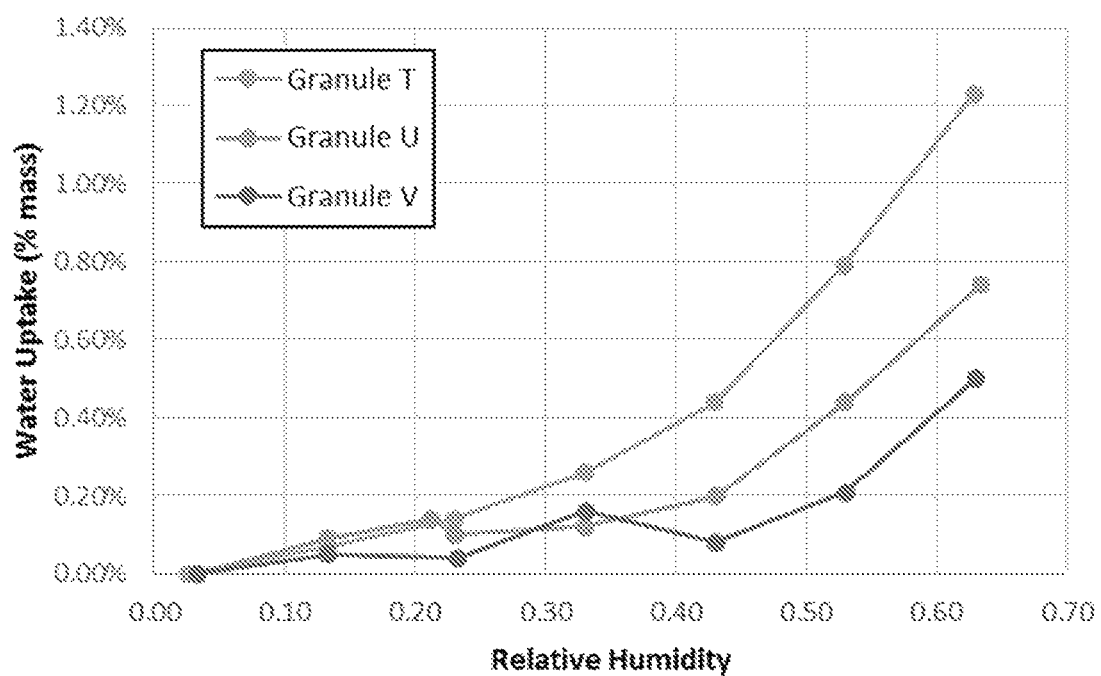

HIGH-PAYLOAD, NON-POROUS, ENZYME-CONTAINING COATED GRANULES AND USE OF SAME

FIELD OF THE INVENTION

The present compositions and methods relate to stable, high-payload, non-porous, enzyme-containing coated granules with improved resistance to activity loss during steam pelleting.

BACKGROUND

The use of enzymes in animal feed is part of modern animal husbandry. Enzymes improve the digestibility of components in animal feed and improve feed conversion. Feed pellets have properties that are favored by the industry when compared with dry feed mixes, such as improved feed quality, decreased pathogens, lower dust levels during manufacture, convenient handling, and more uniform ingredient dosing.

Preferred industry pelleting processes utilize steam injection, in a process known as steam pelleting. Steam pelleting involves conditioning, which adds moisture and elevates the temperature of the feed composition prior to the pelleting step, wherein the steam-heated feed ingredients, or conditioned mash, is forced through a die to form pellets. The pelleting process temperatures are commonly from about 70° C. to 100° C., or higher. The residual activity of enzymes is often significantly reduced during conditioning and subsequent storage. Inactivation may at least be partially reversible if the enzyme reactivates after processing and is irreversible if the catalytic activity does not resume after processing.

The percent recovered activity of an enzyme after steam pelleting is a function of both the inherent thermostability of an enzyme, and the formulation of the enzyme, for example as coated granules. Some enzymes are inherently quite thermostable, so a high recovered enzyme activity need not be attributed to the formulation. However, for any given enzyme one can judge the effectiveness of a formulation by comparing the recovered activity of the formulated enzyme to the unformulated enzyme under a specific set of steam pelleting conditions, e.g. the temperature and time of conditioning.

In order to minimize the cost of raw materials, processing equipment, transport and other handling operations, it is desirable to formulate enzyme granules at the highest possible payload of active enzyme, on a weight basis relative to inactive formulation excipients, such as stabilizers and binders, inactive cores, and coating materials. This has the benefit of reducing the cost of these ingredients relative to the enzyme solids in the formulation. However, existing technologies such as high shear granulation and fluid bed spray coating, by their very nature, place significant constraints on the ability to formulate at very high payloads, Since most commercially available enzyme granules for steam pelleting allocate 50% w/w of more of the formulation space to the required protective coating, this leaves at most about 50% w/w of the final granule available for the enzyme-containing core, including the fermentation solids, and any inert excipients or core materials. In the case of high shear granulation, producing mechanically cohesive, well-formed, enzyme matrix particles by high shear granulation typically requires the addition of high levels of excipients such as polymeric binders, salts, reinforcing fibers, and lubricants. Typically, these excipients consume at least about 80% w/w of the enzyme matrix core, i.e. about 40% of the final coated enzyme granule. Thus, the enzyme-containing fermentation solids in typical high shear granules consume at most about 10% w/w of the final coated granule. Similarly, production of well-formed enzyme granules by fluid bed spray-coating, requires starting with an inert core particle that represents at least about 30% w/w of the final granule, with an additional 5% w/w or so required for excipients that are added to the fermentation solids. After allowing room for the 50% w/w protective coating, this again leaves only about 15% w/w formulation space available for the enzyme-containing fermentation solids. Thus, conventional enzyme granulation technologies are limited to payloads of at most about 10-15% w/w fermentation solids. In practice, most commercial enzyme granules for steam pelleting contain no more than 10% fermentation solids. Feed enzymes produced by fermentation are typically not purified, to minimize cost, and represent at most about 50% w/w of the total fermentation solids. Thus conventional processes used to make feed enzyme granules for steam pelleting, such as high shear granulation and fluid bed spray coating, have an upper payload limit of about 5-8% w/w enzyme solids. Thus, there is a need for a formulations and methods of producing enzyme granules for steam pelleting applications, wherein the payload of the granule is higher than about 10% w/w enzyme solids, or even higher than about 15% w/w enzyme solids.

The fundamentals of making active-agent containing granules for inclusion in animal feed are well known. Contemporary innovation in this technology space necessarily focus on improvements to pelleting stability, and/or recovery, of active ingredients during conditioning. Such improvements provide commercially relevant advantages in a competitive global market. The present compositions and methods are based on the realization that heretofore undescribed and unappreciated composition and process conditions result in a significant increase in pelleting stability.

SUMMARY

The present compositions and methods relate to stable, high-payload, low-porosity, enzyme granules with improved resistance to activity loss during steam pelleting as a result of having particular, well-defined coatings, and methods of use, thereof. Aspects and embodiments of the compositions and methods are described in the following, independently-numbered, paragraphs.

1. In one aspect, an enzyme-containing coated granule is provided, comprising: (a) a payload of at least 10% wt/wt enzyme solids; (b) a continuous protective coating surrounding an enzyme matrix core resulting in a coated granule having (i) a porosity of less than about 0.03 cc/g for macropores within the range of 0.2-8.0 microns in diameter; and (ii) a water uptake of no more than 0.5% w/w water at 60% relative humidity.

2. In some embodiments, the coated granule of paragraph 1 has an enzyme matrix core with a sphericity of at least 0.9.

3. In some embodiments, the coated granule of paragraph 1 or 2 has an enzyme matrix core with a roundness of at least 0.5.

4. In some embodiments, the coated granule of any of the preceding paragraphs has a coating mass fraction of at least 30% w/w.

5. In some embodiments, the coated granule of any of the preceding paragraphs has a coating mass fraction of less than 70% w/w.

6. In some embodiments of the coated granule of any of the preceding paragraphs, the water activity of the core is less than 0.2.

7. In some embodiments of the coated granules of any of the preceding paragraphs, the critical relative humidity of the coating is greater than 60%.8.

8. In some embodiments of the coated granules of any of the preceding paragraphs, the coating comprises non-hygroscopic materials and has a water uptake of no more than 0.5% w/w water at 60% relative humidity.

9. In some embodiments, the coated granule of any of preceding paragraphs has a coating comprising no more than 60% salt (w/w).

10. In some embodiments, the coated granule of any of the preceding paragraphs has a coating comprising no less than 30% salt (w/w).

11. In some embodiments of the coated granule of any of the preceding paragraphs, the core comprises less than 20% excipients (w/w).

12. In some embodiments, the coated granule of any of the preceding paragraphs has an overall diameter of greater than 100 μm.

13. In some embodiments, the coated granule of any of the preceding paragraphs has an overall diameter of less than 400 μm.

14. In some embodiments, the coated granule of any of the preceding paragraphs, the enzyme matrix core is made by spray granulation.

15. In some embodiments of the coated granules of any of the preceding paragraphs, the enzyme solids comprise a phytase.

16. In another aspect, a method for increasing the stability of an enzyme in a composition, or the recovery of enzyme in a steam pelleting process is provided, the method comprising providing the enzyme in coated granules comprising: (a) a payload of at least 10% wt/wt enzyme solids; (b) a continuous protective coating surrounding an enzyme matrix core resulting in a coated granule having (i) a porosity of less than about 0.03 cc/g for macropores within the range of 0.2-8.0 microns in diameter; and (ii) a water uptake of no more than 0.5% w/w water at 60% relative humidity.

17. In some embodiments of the method of paragraph 16, the enzyme matrix core has a sphericity of at least 0.9.

18. In some embodiments of the method of paragraph 16 or 17, the enzyme matrix core has a roundness of at least 0.5.

19. In some embodiments of the method of any of paragraphs 16-18, the granule has a coating mass fraction of at least 30% w/w.

20. In some embodiments of the method of any of paragraphs 16-19, the granule has a coating mass fraction of less than 70% w/w.

21. In some embodiments of the method of any of paragraphs 16-20, the water activity of the enzyme matrix core is less than 0.2.

22. In some embodiments of the method of any of paragraphs 16-21, the critical relative humidity of the coating is greater than 60%.

23. In some embodiments of the method of any of paragraphs 16-22, the coating comprises non-hygroscopic materials and has a water uptake of no more than 0.5% w/w water at 60% relative humidity.

24. In some embodiments of the method of any of paragraphs 16-23, the coating comprises no more than 70% salt (w/w).

25. In some embodiments of the method of any of paragraphs 16-24, the coating comprises no less than 30% salt (w/w).

26. In some embodiments of the method of any of paragraphs 16-25, the core comprises no more than 30% excipients (w/w).

27. In some embodiments of the method of any of paragraphs 16-26, the granule has an overall diameter of greater than 100 μm.

28. In some embodiments of the method of any of paragraphs 16-27, the granule has an overall diameter of less than 400 μm.

29. In some embodiments of the method of any of paragraphs 16-28, the enzyme matrix core is made by spray granulation.

30. In some embodiments of the method of any of paragraphs 16-29, the granule is made by spray granulation.

31. In some embodiments of the method of any of paragraphs 16-30, the granule has a water soluble or dispersible coating comprising a wax or a hydratable salt.

32. In some embodiments of the method of any of paragraphs 16-31, the enzyme solids comprise a phytase.

33. In another aspect, a pelleted animal feed composition comprising the granule of any of paragraphs 1-15 is provided.

These and other aspects and embodiments of the compositions and methods will be apparent from the present description and drawings.

BRIEF DESCRIPTION OF THE DRAWINGS

FIG. 1 is a graph showing water uptake versus relative humidity for various high-payload granules described in the Examples.

DETAILED DESCRIPTION OF THE INVENTION

I. Definitions and Abbreviations

Prior to describing the present strains and methods in detail, the following terms are defined for clarity. Terms not defined should be accorded their ordinary meanings as used in the relevant art.

As used herein, the term "granule" refers to a small compact particle of a substance. The particle comprises a core with one or more optional coating layers.

As used herein, the term "core" is interchangeable with the term "seed" and comprises the unitary inner part of a granule upon which additional coatings or layers can be applied. A core may comprise a single material such as a salt or sugar crystal, or may be composed of a mixture of materials. A core may be inert or may comprise on or more enzymes, either as pure enzyme or enzyme mixed or embedded within a matrix of inert materials.

As used herein, the term "enzyme matrix core" refers to a granule core comprising enzyme. An enzyme matrix core may further comprise fermentation solids and excipients, such as binders and fillers. The active enzyme is dispersed or dissolved throughout the enzyme matrix core, and is not layered upon a unitary inert core devoid of enzyme.

As used herein, the term "multi-layered granule" refers to a composition comprising a core and at least one coating layer. The core may be an inert core or an enzyme matrix core.

As used herein, the term "coating layer" and "layer" are interchangeable. The coating layer(s) generally encapsulates the core in order to form a substantially continuous layer so that the core surface has few or no uncoated areas. The materials (e.g., the agents, components and enzyme detailed herein) used in the granule and/or multi-layered granule are suitable for the use in foods and/or animal feeds. The materials can be food grade or feed grade.

As used herein, the term "outer coating layer" refers to the coating layer of the multi-layered granule that is the furthest from the core (i.e., the last coating layer that is applied).

As used herein, the term "enzyme coating layer" or "enzyme layer" refers to an enzyme layer that comprises at least one enzyme.

As used herein, "porosity" is a measure of the void volume, or volume contained in empty spaces, in a material, per unit of mass of the material. As a caveat, some tests effectively measure the "accessible void" that is accessible from the surface of a material, and do not measure any internal void space.

As used herein "non-porous" or "low porosity" refers to a coating, coated granule, or other material with a macropore porosity of less than about 0.03 cc/g, as determined by mercury intrusion porosimetry (MIP).

As used here, a "macropore," in the context of porosity, refers to a pore with a diameter between 0.2 and 8 microns, as determined by mercury intrusion porosimetry (MIP).

As used herein, "macropore porosity" refers to porosity of only macropores, i.e. that portion of pores in a solid that have a diameter between 0.2 and 8.0 microns, as determined by mercury intrusion porosimetry (MIP).

As used here, "continuous," with respect to a granule coating, means uninterrupted by breaks, cracks, or holes, such that that the properties of the contiguous portions of the coating control the properties of a coating, as opposed to breaks, cracks, or holes in the coating. The continuity of a coating can be assessed by observing a representative sample of granules under scanning electron microscope (SEM).

As used herein, "roundness" refers to Krumbein roundness, a measure of how closely the external angularity of an object approaches that of a mathematically perfect circle, in accordance with the set of exemplary image standards established by Krumbein (Krumbein, W. C. (1941) *J Sediment. Petrol.* 11:64). Roundness is measured on a scale of 0 to 1. A highly angular object with many sharp corners or protrusions will have a roundness value close to 0, while a smooth object with few sharp corners will have a roundness value close to 1. Roundness values in accordance with the Krumbein image standards can be measured on a sample of particles using an optical morphology instrument with image analysis software, such as a Retsch Camsizer XT, Malvern Morphologi G3, or Microtrac PartAn 3-D.

As used herein, "sphericity" is a measure of how closely the shape of an object approaches that of a mathematically perfect sphere, formally defined as the cube root of the ratio of the volume of an object to the volume of the smallest sphere that contains it completely. Sphericity is measured on a scale of 0 to 1. A highly elongated object will have a sphericity value close to 0, while a compact or spherical object will have a sphericity value close to 1. Sphericity can be measured on a sample of particles using an optical morphology instrument with image analysis software, such as a Retsch Camsizer XT, Malvern Morphologi G3, or Microtrac PartAn 3-D.

As used herein, "weight percent," "weight fraction," "mass fraction" or simply "fraction" refers to the relative amount of mass on a % wt/wt or fractional wt/wt basis, for example, the relative amount of mass of a coating compared to the mass of an entire granule.

As used herein, "water activity (aw)" is defined as the partial vapor pressure of water in a substance divided by the standard state partial vapor pressure of water at a given temperature. It is a measured characteristic of a solid or liquid in equilibrium with a surrounding atmosphere.

As used herein, "relative humidity (RH)" is the ratio of the partial pressure of water vapor to the equilibrium vapor pressure of water at a given temperature.

As used herein, "critical relative humidity (CRH)" of a salt is defined as the relative humidity of the surrounding atmosphere (at a certain temperature) at which the material begins to absorb moisture from the atmosphere and below which it will not absorb atmospheric moisture.

As used herein, "water uptake" is the weight percent of water absorbed by a solid after equilibration to a surrounding atmosphere at a given relative humidity.

As used herein, the term "fermentation solids" refers to dried or partially dried solids derived from a microbial fermentation broth that is processed so as to recover one or more useful bioactives of interest, such as an enzyme. Fermentation solids can be derived from whole cell broth obtained directly from a fermenter, from clarified broth with cells removed by filtration or centrifugation, concentrated, e.g., by ultrafiltration or evaporation, or purified to varying degrees, e.g., by chromatography, precipitation or crystallization. Fermentation solids can thereby include impurities other than the enzyme actives, such as inactive protein, peptides, amino acids, polysaccharides, sugars, salts and other residual compounds formed during fermentation and downstream processing. Fermentation solids may also comprise some residual free or bound water remaining after a drying or granulation process. Fermentation solids do not include excipients, which are defined separately (infra).

As used herein, "enzyme solids" refers to dried or partially dried solids comprising one of or more active enzymes. It is understood that fermentation solids can comprise enzyme solids in whole or in part, i.e., fermentation solids can comprise significant amounts of impurities in addition to enzyme solids. Enzyme solids comprise all active enzyme of interest in the composition, but exclude minor or inadvertent enzymatic activities that may be present but in any case comprise less than 5% of total enzyme solids present in the fermentation solids within the enzyme matrix core.

As used herein, "payload" refers to the mass fraction of a material of interest within a granule. The material of interest, within the scope of this invention, is either fermentation solids in aggregate, or only enzyme solids, depending on the context specified. Payload is expressed as % wt/wt solids of either fermentation solids or enzyme solids relative to the total mass of the granule. In this manner, one can also refer to "enzyme payload" or "fermentation solids payload."

As used herein, the term "excipients" refers to solids added to fermentation solids during or after processing but prior to drying or granulation, in order to improve the stability, handling, or physical properties of the resulting dry granules. In this use, excipients are not counted within the enzyme payload or fermentation solids payload of a granule. Excipients include, but are not limited to: stabilizers, binders, viscosity modifiers, surfactants, fillers, lubricants, desiccants, humectants, pigments and the like.

As used herein, "low hygroscopicity" or "non-hygroscopic" refers to a material that takes up no more than 0.5% w/w water at 60% relative humidity, as measured via dynamic vapor sorption or an equivalent method.

As used herein, a "wax" is defined as any hydrocarbon, fatty acid, fatty alcohol, or salt or ester thereof, that is insoluble in water but soluble in non-polar organic solvents. A comprehensive definition of wax has been drawn up in Europe by the Deutsche Gesellschaft für Fettwissenschaft (DGF, German Association for Fat Science). According to this definition, waxes (i) have a drop point or melting point above 40° C. (ii) melt without decomposition; (iii) have melt viscosities not exceeding 10,000 mPa s at 10° C. above the melting point, (iv) exhibit strongly negative temperature dependence in terms of viscosity and do not tend toward stringiness above the melting point, (v) are polishable under slight pressure and have a strongly temperature-dependent consistency and solubility, (vi) are kneadable or hard to brittle, coarse to finely crystalline, transparent to opaque, but not glassy, or highly viscous or liquid at 20° C., (vii) melt between 50° and 90° C. (special waxes, as used in the present compositions and methods, melt at temperatures as high as 200° C.), and form pastes or gels and are poor conductors of heat and electricity (i.e., they are thermal and electrical insulators).

As used herein, the terms "pellets" and "pelleting" refer to solid, rounded, spherical and cylindrical tablets or pellets and the processes for forming such solid shapes, particularly feed pellets and solid, extruded animal feed. Known animal feed pelleting manufacturing processes generally include admixing together feed ingredients for about 1 to about 5 minutes at room temperature, transferring the resulting admixture to a surge bin, conveying the admixture to a steam conditioner, optionally transferring the steam conditioned admixture to an expander, transferring the admixture to the pellet mill or extruder, and finally transferring the pellets into a pellet cooler. Fairfield, D. 1994. Chapter 10, Pelleting Cost Center. In Feed Manufacturing Technology IV. (McEllhiney, ed.), American Feed Industry Association, Arlington, VA, USA, pp. 110-139.

As used herein, the term "heat-treated animal feed pellets" refers to admixtures of ground feed grains, e.g. corn or soy, and supplemental additives such as vitamins, lipids and enzymes, that are subjected to a heat treatment (such as steam conditioning), typically at a temperature of at least 90° C. for at least 30 seconds. The admixture can then be extruded to form the animal feed pellets.

As used herein, the term "stability" refers to any of a variety of effects in which the enzymatic activity or other functional property of a feed complementing (or supplementing) enzyme is beneficially maintained or improved. The feed enzyme can exhibit stability by showing any of improved "recovered activity," "thermostability," and/or "inactivity reversibility." "Stability" can refer to activity maintained in enzyme composition either prior to or after combination with feed or feed pellets. Non-exclusive examples of feed enzyme are amylases, phytases, proteases, and xylanases.

As used herein, the term "recovered activity" or "activity recovery" refers to the ratio of (i) the activity of a feed enzyme after a treatment involving one or more of the following stressors: heating, increased pressure, increased pH, decreased pH, storage, drying, exposure to surfactant(s), exposure to solvent(s), and mechanical stress) to (ii) the activity of the enzyme before the treatment. The recovered activity may be expressed as a percentage. The percent recovered activity is calculated as follows:

$$\% \text{ recovered activity} = \frac{\text{(activity after treatment)}}{\text{(activity before treatment)}} \times 100\%$$

As used herein, an "FTU" or "phytase turnover unit" or "unit of phytase activity" or "Unit" is the amount of enzyme that is able to release 1 μmol inorganic phosphate per minute. Phytase activity is assayed according to Association of Analytical Chemists (AOAC) Official Method 2000.12, as described in "Determination of phytase activity in feed by a colorimetric enzymatic method: collaborative interlaboratory study" Engelen, A. J. et al. (2001) JAOAC Int. 84:629-33. Briefly, the ground samples are extracted in 220 mM sodium acetate trihydrate, 68.4 mM calcium chloride dehydrate, 0.01% Tween 20, pH 5.5. The supernatant is then assayed. The assay measures the release of inorganic phosphate from rice phytase, at pH 5.5, for 60 min at 37° C. The assay is stopped with acidic molybdate/vanadate reagent, and phosphate is quantified by intensity of yellow colored complex of the vanadomolybdophosphoric acid.

As used herein, the term "about" refers to +15% to the referenced value.

For ease of reference, elements of the present compositions and methods may be arranged under one or more headings. It is to be noted that the compositions and methods under each of the headings also apply to the compositions and methods under the other headings.

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

| | |
|---|---|
| ° C. | degrees Centigrade |
| cc | cubic centimeter |
| CFM | cubic feet per minute |
| $D_{50}$ | diameter of median particle (volume basis) |
| FTU/g | phytase units/gram |
| g or gm | gram |
| g/L | grams per liter |
| g/mol | grams per mole |
| mol/mol | mole to mole ratio |
| hr or h | hour |
| kg | kilogram |
| M | molar |
| mg | milligram |
| mL or ml | milliliter |
| min | minute |
| mM | millimolar |
| μm | micrometer (micron) |
| μmol | micromole |
| UFC | ultrafiltered concentrate |
| SEM | scanning electron microscopy/microscope |
| % wt/wt | weight percent |

II. Non-Porous Enzyme Granules

The present compositions and methods pertain to stable, high-payload, non-porous enzyme granules with improved resistance to activity loss during steam pelleting by virtue of their shape and coating characteristics. High-payload granules are clearly desirable as a means of reducing the cost of granular enzymes. There are previous disclosures of high-payload enzyme granules, but none of the granules have demonstrated high stability in a steam pelleting process combined with having the small particle size needed to ensure good distribution of enzyme when granules are blended into solid products. High-payload granules have been made with thick coatings, but the present inventors have found that thick coatings do not ensure adequate protection against steam treatment. Nor can the coating composition alone guarantee success.

The present compositions and methods are directed to granules with three critical features, specifically:
(a) a payload of at least 10% enzyme solids;
(b) a continuous protective coating having a macropore porosity of less than about 0.03 cc/g; and
(c) a water uptake of no more than 0.5% at 60% RH.

Porosity, in terms of specific pore volume of a particle, can be measured by mercury intrusion porosimetry (MIP), using a penetrometer, as described, herein. Surprisingly, not all sizes of pores are relevant to achieving the aims of the invention; the specific volume of pores with diameters smaller than 0.2 μm or larger than 8.0 μm do not correlate with steam resistance. Pores within the defined diameter range of 0.2 to 8.0 μm are herein referred to as "macropores," and the specific volume of these macropores in the coated enzyme granule is the essential feature that provides for excellent pelleting stability.

Mercury intrusion porosimetry was conducted on the samples to assess porosity in the 0.003-400 μm region. Outgassed samples were charged to the calibrated penetrometer cell of the Micromeritics AutoPore III. The penetrometer was sealed, installed in the instrument and placed under vacuum. Mercury was admitted to the penetrometer at gradually increasing pressure from 0-413 MPa (0-60,000 psia) and intrusion was recorded (64 data points) and analyzed via the Washburn Equation with a contact angle value of 1300 and surface tension of 478 dyne/cm to generate a pore-size/volume distribution. To assess sample stability, a series of mercury intrusion/extrusion experiments were conducted on the instrument to evaluate reproducibility/hysteresis.

To be considered as having "low porosity" or being "non-porous," the coated granules must have a macropore porosity of less than about 0.03 g/cc. Low porosity can be achieved, for example, by the combination of two features: (a) a smooth enzyme matrix core with a sphericity of at least 0.9, or alternatively or additionally a roundness of 0.5; and (b) a coating mass fraction of at least 30% w/w. Both features appear to be required; having only one of the two features is not sufficient to make granules non-porous. Although each of these individual features have been disclosed in the prior art, the importance of the combination of both features to coating porosity, and its effect on steam stability, is nowhere described. Additionally, by applying the continuous coating over a spherical, round core, a non-porous granule can be obtained that have less than about 70% w/w coating mass fraction. Thus, only a moderately thick coating is required, enabling high net payloads and limiting the cost and time required to ensure adequate protection of the enzyme in the coated granule.

Several features distinguish the present compositions and methods from those previously described. For example, AXTRAPHY® 20000 TPT2® (DuPont Industrial Biosciences), RONOZYME® HiPhos GT (Novozymes/DSM), and other granules are low-porosity granules that also show acceptable steam survivability. However, these granules rely on large quantities of binders and coatings, or embedding of the enzyme protein as a minor component within a matrix, to confer steam survivability. For example, the protein payload of the RONOZYME granule is approximately 1-2% w/w with the amount of phytase being roughly 0.5-1% w/w. US Patent Pub. No. 20030124224 (DSM), describes particles having high enzyme payloads, but provides no suggestion or demonstration of how to coat these particles to make them thermostable. For example, the uncoated phytase enzyme particles exemplified in the patent publication are unprotected and are not suitable for steam pelleting. By contrast, the present granules have a small size and high payload and must rely on a relatively thin coating to confer adequate protection during steam pelleting. Low porosity has been found critical to meeting this objective.

III. Cores for Non-Porous Granules

A feature of the present compositions and methods is a high-payload, enzyme matrix core. The present granule does not have an inert core, around which enzyme must be layered, but rather comprises a unitary enzyme matrix core, in which enzyme and other fermentation solids (including enzyme solids) occupy the central part of the granule. In some embodiments, the fermentation solids comprise the majority of the core, while excipients, which are conventionally added to protect enzymes, are only minor components of the core, e.g., comprising at most 15%, 20%, or 25% of the core. By this means, and other enabling features of the core and coating such as shape and porosity, the granule payload is maximized by eliminating the need for inactive, inert materials that would otherwise consume valuable "real estate" in the formulation, thus reducing the potential payload of active enzyme and other fermentation solids.

Furthermore, it is a surprising aspect of the invention that it is thereby possible to produce such low-excipient-containing, high-payload enzyme matrix cores of the required spherical shape, suitable for the application of continuous, non-porous coatings, without the need to start with an inert core or seed. In prior art processes such as spray-coating, the size, shape, smoothness, density and fluidization characteristics of the inert core or seed particle play a critical role in serving as a "template" or starting point to ensure the deposition of subsequent continuous laying of enzyme layers and other coating layers. Similarly, it is a surprising feature that it is possible to build an enzyme granule that protects enzyme under adverse storage or handling conditions such as humid environments or steam pelleting process by starting from a matrix particle that comprises mostly enzyme and fermentation solids, but only a minor percentage of excipients, by attending to the shape of the matrix particle and the porosity of the coating. Prior art matrix granules have provided protection largely through the use of a high level of protective excipients within the core, without attending to the shape of the core, or by application of thick coatings, without attending to the porosity of those coatings.

The enzyme matrix core comprises enzyme, either pure or in combination with other fermentation solids, and excipients. Excipients are solids added to fermentation solids during or after processing but prior to drying or granulation, in order to improve the stability, handling, or physical properties of the resulting dry granules, and can include stabilizers, binders, viscosity modifiers, surfactants, fillers, lubricants, desiccants, humectants, pigments and the like. Preferred excipients are non-hygroscopic forms of binder polymers, clays, and minerals. Preferred excipients include but are not limited to polymers, such as polyvinyl alcohol and polyvinylpyrrolidone, insoluble clays and minerals, such as kaolin, talc, and calcium carbonate, and anhydrous or low-hydration salts, such as sodium sulfate, sodium chloride, magnesium sulfate, zinc sulfate, and ammonium sulfate The size of the core is important to the size of the final granules, which is important to the uniformity of distribution of protein of interest in a feed product containing the final granules. Smaller granules ensure more uniform distribution than large particles. Preferred particles have an average diameter of less than 600 µm, less than 550 µm, less than 500 µm, less than 450 µm, less than 400 µm, less than 350 µm, less than 300 µm, or even less than 250 µm, with a lower limit of about 100 µm. The lower limit excludes fine particles and spray-dried powder, which include particles that are not sufficiently spherical and cannot be coated to achieve the present objectives.

It has been discovered that the shape of the core has a significant impact on the properties of the final granule, even one coated with a low-porosity coating. Preferred cores have a sphericity of at least 0.9, for example, at least 0.90, at least 0.91, at least 0.92, at least 0.93, at least 0.94, at least 0.95, at least 0.96, at least 0.97, or even at least 0.99. Alternatively, or additionally, preferred cores have a roundness of at least 0.5, at least 0.6, at least 0.7, or even at least 0.8.

Average diameter, sphericity, roundness, and other core properties can be measured by many methods, such as using scanning electron microscopy of samples of combined with basic mechanical measurements, i.e., applying a simple ruler to a sufficient number of electron micrographs to obtain a statistically relevant number. Image processing software can also be used to automate this process.

The present granules have high payloads, comprising at least 25%, at least 30%, or even at least 35% wt/wt fermentation solids, and/or at least 10%, at least 15%, or even at least 20% enzyme solids.

IV. Coatings for Low Porosity Granules

The enzyme-containing matrix core is coated with at least one non-porous, water-soluble or dispersible, coating layer. Preferably, the coating is non-hygroscopic. The materials used in the coating layer(s) should be suitable for use in foods and/or animal feeds (see, e.g., US20100124586, WO9932595 and U.S. Pat. No. 5,324,649). The coating should be continuous, i.e., characterized by the absence of gaps, cracks, and/or holes that would render the micronscale porosity of the coating irrelevant to protecting the core. In some embodiments, the enzyme-containing matrix core is coated with only a single coating.

The coating layer may include one or more of the following materials: an inorganic salt (e.g., sodium sulfate, sodium chloride, magnesium sulfate, zinc sulfate, and ammonium sulfate), citric acid, a sugar (e.g., sucrose, lactose, glucose, and fructose), a plasticizer (e.g., polyols, urea, dibutyl phthalate, and dimethyl phthalate), fibrous material (e.g., cellulose and cellulose derivatives such as hydroxypropyl-methyl cellulose, carboxy-methyl cellulose, and hydroxy-ethyl cellulose), clay, nonpareil (a combination of sugar and starch), silicate, phosphate, starch (e.g., corn starch), fats, oils (e.g., rapeseed oil, and paraffin oil), lipids, vinyl polymers, vinyl copolymers, polyvinyl alcohol (PVA), plasticizers (e.g., polyols, urea, dibutyl phthalate, dimethyl phthalate, and water), anti-agglomeration agents (e.g., talc, clays, amorphous silica, and titanium dioxide), anti-foam agents (such as FOAMBLAST 882® and EROL 6000K®), and talc. US20100124586, WO9932595, and U.S. Pat. No. 5,324,649 detail suitable components for the coating layers.

In some embodiments, the coating layer comprises sugars (e.g., sucrose, lactose, glucose, granulated sucrose, maltodextrin and fructose). In some embodiments, the coating layer comprises a polymer such as polyvinyl alcohol (PVA). Suitable PVA for incorporation in the coating layer(s) of the multi-layered granule include partially hydrolyzed, fully hydrolyzed and intermediately hydrolyzed having low to high degrees of viscosity. In some embodiments, the coating layer comprises an inorganic salt, such as sodium sulfate.

The coating layer should be non-hygroscopic with a water uptake of no more than 0.5% w/w water at 60% relative humidity, as measured via dynamic vapor sorption (DVS) or an equivalent method. A hygroscopic coating will tend to absorb water during storage in the presence of humidity, or during exposure to steam, as in the steam pelleting of animal feed. Uptake of water will tend to further increase the porosity or permeability of a coated particle to moisture in a manner that is not captured by porosimetry measurements. Mercury intrusion porosimetry (MIP) requires the use of dry samples, and hence cannot take into account this permeabilizing effect of absorbed water. Non-hygroscopic coatings are readily formulated by skilled persons, selecting and combining materials that individually demonstrate low moisture uptake by DVS, i.e. a water uptake of no more than 0.5% w/w water at 60% relative humidity. It is straightforward to produce moisture sorption isotherms for candidate coating materials, alone or in combination, using DVS. Sorption isotherms for many materials are published in the literatures of food science, polymer science and materials science. Examples of non-hygroscopic materials according to the definition include sodium sulfate, sodium chloride, calcium carbonate. Examples of hygroscopic materials include sucrose, dextrin, starch, disodium monophosphate, and zinc sulfate.

The coating layer should be selected such that the granule has a macropore porosity of less than about 0.03 cc/g as determined by mercury intrusion porosimetry (MIP), using a penetrometer, as described, herein. Examples of porosity values are less than about 0.030 cc/g, less than about 0.028 cc/g, less than about 0.026 cc/g, less than about 0.024 cc/g, less than about 0.022 cc/g, less than about 0.020 cc/g, less than about 0.018 cc/g, less than about 0.016 cc/g, less than about 0.014 cc/g, less than about 0.012 cc/g, less than about 0.010 cc/g, and even less than about 0.008 cc/g.

In some embodiments, the coating layer is selected such that the granule has a critical relative humidity of greater than 50%, greater than 60%, greater than 70%, or even greater than 80%. In some embodiments, the coating layer comprises non-hygroscopic materials and has a water uptake of no more than 0.5% wt/wt, no more than 0.4% wt/wt, and even no more than 0.3% wt/wt at 60% relative humidity.

In some embodiments, the mass fraction of the coating relative to the entire granule is at least 30%, at least 40%, or more (w/w). In some embodiments, the mass fraction of the coating is less than 50% (w/w).

In some embodiments, the coating comprises at least 30% salt (w/w). In some embodiments, the coating comprises less than 60% salt (w/w).

V. Production of Enzyme Matrix Cores

High payload enzyme matrix cores may be made by any process that can produce well-formed, spherical, round particles suitable for application of continuous, non-porous coatings, without the need for more than about 20% added formulation ingredients such as excipients or core materials. In a preferred embodiment, the process used to produce high payload enzyme matrix cores is spray granulation, sometimes known as spouted bed granulation, in which enzyme matrix cores are built up by spraying fermentation solids and excipients into a fluidized bed, first forming spray dried particles as nuclei, and subsequently building up particles of increasing diameter by further spraying and layering onto the starting nuclei, without the need for an initial inert core.

An example of equipment suitable for spray granulation is the Glatt ProCell system, available from Glatt GmbH (Binzen, Germany). Processes that require high levels of inactive excipients or core materials, in excess of above 20-30% w/w of the enzyme matrix core, in order to produce well-formed particles suitable for application of continuous, non-porous coatings, are not suitable processes for the invention. Such processes not suitable for the invention include, but are not limited to: spray drying, fluid bed spray coating, fluid-bed agglomeration, high shear granulation, extrusion, spheronization, rotary atomization, prilling, crystallization, and roll compaction. Such processes are unlikely to produce suitable enzyme matrix cores.

VI. Specific Proteins of Interest for Inclusion in the Present Granules

Numerous proteins of interest are suitable for inclusion in the present granules. It should be understood that the payload of the granules may defined by the amount of total protein contained within the granules, which ideally includes a specific protein of interest. Many protein compositions that contain proteins of interest are homogenous or "impure," being highly enriched for a specific protein of interest but containing other proteins, cell lysate, or even whole intact cells. As described within, the present granules require at least 25% wt/wt fermentation solids, or at least 10% enzyme solids, which include a protein of interest.

The exemplified enzyme of interest is a variant *Buttiauxella* phytase, but phytases are by no means the only enzymes protectable by the present granules. Any enzyme that is subjected to steam pelleting is encompassed by the present description, including for example, acyl transferases, α-amylases, β-amylases, α-galactosidases, arabinosidases, aryl esterases, β-galactosidases, carrageenases, catalases, cellobiohydrolases, cellulases, chondroitinases, cutinases, endo-β-1, 4-glucanases, endo-β-mannanases, esterases, exomannanases, galactanases, glucoamylases, hemicellulases, hyaluronidases, keratinases, laccases, lactases, ligninases, lipases, lipoxygenases, mannanases, oxidases, oxidoreductases, pectate lyases, pectin acetyl esterases, pectinases, pentosanases, perhydrolases, peroxidases, peroxygenases, phenoloxidases, phosphatases, phospholipases, polygalacturonases, proteases, pullulanases, reductases, rhamnogalacturonases, glucanases, tannases, transglutaminases, xylan acetyl-esterases, xylanases, xyloglucanases, xylosidases, metalloproteases, serine proteases, and combinations, thereof.

VII. Additional Uses

While the present granules have been described for use in applications involving steam pelleting, they are no doubt useful in applications, particularly those involving stressful moist environments. Such environments include aqueous liquids as well as dry solids that are subjected to even moderate humidity during storage. Particular examples of such applications include solid and liquid laundry detergent formulations and automatic dishwashing formulations.

VIII. Combinations of Various Embodiments

Embodiments of the compositions and methods that are described, herein, including those described under different section headings, and other embodiments that would be apparent to the skilled person, can be combined unless the combination would defeat the asserted purposes and advantages of the present compositions and methods.

EXAMPLES

Example 1. Porosity and Steam-Stability Trends in High-Payload Granules

A liquid enzyme UFC from *Trichoderma reesei* host cells expressing a variant of a phytase from a *Buttiauxella* sp. was produced using standard methods. Of the total protein, the concentrate contained about 40% wt/wt phytase based on activity. Solid enzyme matrix cores were produced using several different formulation methods and excipients. These solid enzyme matrix cores were subsequently coated in a batch fluid bed coater with a variety of moisture-resistant coatings comprising one or more sprays containing polyvinyl alcohol, talc, dextrin and sodium sulfate. Among all of the finished granules, the total fermentation solids contained in the enzyme matrix cores ranged from 20-60% wt/wt of the finished granules, corresponding to 6-25% wt/wt phytase enzyme, based on activity. The coatings accounted for 40-80% wt/wt of the finished granules. The phytase activity of the finished granules ranged from 40,000-100,000 FTU/g.

The granules were pelleted with animal feed on a test pellet mill, with a conditioning time of 30 s at a temperature of 95° C. All high-payload granules with a macropore volume of 0.03 cc/g or less showed a pelleting recovery of about 70% or greater, with the lowest macropore volumes typically correlating with the highest activity recoveries. All high-payload granules that had a pelleting recovery above 80% had a macropore volume of 0.02 cc/g or lower. All high-payload granules that showed a pelleting recovery of less than 60% had a macropore volume of 0.04 cc/g or greater. The trends are indisputable and are scientifically and commercially relevant.

Granules were additionally subjected to a laboratory-scale steaming test, with a conditioning time of 12 s in 100° C. saturated steam. All high-payload granules with a macropore volume of 0.02 cc/g or less showed a laboratory-scale steaming recovery of about 80% or greater, with the lowest macropore volumes typically correlating with the highest activity recoveries. All high-payload granules that showed a laboratory-scale steaming recovery of less than about 70% had a macropore volume of about 0.04 cc/g or greater.

Example 2. Comparison of Enzyme Matrix Cores Produced Using Various Methods A UFC containing phytase was produced as before. Solid enzyme matrix cores were produced using several different granulation methods and excipients, and these solid enzyme matrix cores were subsequently coated with a moisture-resistant coating. The cores for Granules A and B were produced by roll compaction on a Fitzpatrick CCS220 unit with up to 60% wt/wt excipients added to the fermentation solids. The cores for Granules C and D were produced by continuous fluid-bed spray agglomeration on a Glatt WST-5 Fluid Bed Coater with less than 10% wt/wt excipients added to the fermentation solids. The cores for Granules E and F were produced by continuous fluid-bed spray granulation on a Glatt ProCell 5 Lab System unit with less than 10% wt/wt excipients added to the fermentation solids.

Each set of cores was individually sieved to a size range of 150-425 μm and subsequently coated in a batch fluid bed on a Vector VFC-LAB 1 unit. The coating of each granule included a salt layer (sodium sulfate) and a hydrophobic layer (PVA/talc) that together comprised 55-65% wt/wt of the granule. The batch size for each granule was 1-2 kg. The salt layers were sprayed from an aqueous solution containing 20-30% wt/wt sodium sulfate at a bed temperature between 40-50° C. and a rate between 20-30 g solution/min. The hydrophobic layers were sprayed from an aqueous suspension containing a total of 15-25% wt/wt talc and PVA at a bed temperature between 50-55° C. and a rate between 5-15 g suspension/min. The talc and PVA were mixed in a mass ratio of about 2:1. The flowrate of air used to fluidize the bed was between 20-50 CFM, depending on the total mass of the bed. Spray parameters were adjusted as needed to minimize either agglomeration of the bed or spray-drying of the coating solids. The resulting granules exhibited phytase activity in the range of 40,000-100,000 FTU/g.

The steam stability of the granules was subsequently tested using two methods. First, the granules were exposed to 100° C. saturated steam for 12 s on a lab scale steam stability tester. Second, the granules were pelleted with corn and soy mash on a typical animal feed pellet mill, using a conditioning time of 30 s and a feed conditioning temperature of 95° C.

The porosities, particle sizes, and steam stability information for the granules are summarized below, in Table 1, which further includes observations on particle morphology based on SEM images. The last row of the table (and all subsequent tables) identifies whether the described formulation falls within the present compositions and methods.

porosity in the desired range of 0.03 cc/g or less, and these granules exhibit the greatest steam stability. The cores produced using spray agglomeration showed the least regularity under SEM. The macropore porosity of these cores was not reduced to the desired range by spray coating, likely due to the challenging morphology.

The performance of the cores does not correlate with the quantity of excipients used or the concentration of phytase in the granule. Rather, it is the quality of the coating, as revealed by porosity measurements, that correlates with the highest steam stability. An appropriate high-payload core production method must be selected in order to enable a low-porosity coating and stability to high-temperature steam conditions.

Example 3. Coating of Different Spray Granulated Phytase Granules

Even when the same core generation method is used, it is important to control the parameters of production in order to obtain a granule that can be coated with a low-porosity coating. Table 2, below, summarizes physical properties and steaming performance for two coated phytase granules, designated G and H. The sphericity and roundness of the cores was measured using a Retsch Camsizer XT instrument and its included image processing software, analyzing at least 10,000 individual particles for each sample. The cores of granules G and H were produced from a UFC containing

TABLE 1

Steam stability of various granules produced by different methods

|  | Granule A | Granule B | Granule C | Granule D | Granule E | Granule F |
|---|---|---|---|---|---|---|
| Core production method | Roll compact. | Roll compact. | Spray agglom. | Spray agglom. | Spray granul. | Spray granul. |
| Core appearance | Jagged prisms | Jagged prisms | Lumpy agglomerates | Lumpy agglomerates | Bumpy sphere | Smooth sphere |
| Granule core fraction (% wt/wt) | 35 | 50 | 40 | 40 | 40 | 45 |
| Granule salt coating fraction (% wt/wt) | 54 | 39 | 49 | 49 | 49 | 44 |
| Granule hydrophobic coating fraction (% wt/wt) | 11 | 11 | 11 | 11 | 11 | 11 |
| Total fermentation solids (% wt/wt) | 15 | 20 | 36 | 36 | 40 | 41 |
| Enzyme solids (% wt/wt) | 6 | 8 | 14 | 14 | 16 | 17 |
| Enzyme core macropore porosity for 0.2-8.0 µm macropores (cc/g) | 0.161 | 0.149 | 0.057 | 0.048 | 0.011 | 0.031 |
| Coated granule macropore porosity for 0.2-8.0 µm macropores, (cc/g) | 0.073 | 0.037 | 0.074 | 0.064 | 0.010 | 0.010 |
| Granule D50, µm | 410 | 330 | 370 | 410 | 430 | 470 |
| Lab-scale activity recovery after 12 s (%) | 8 | 65 | 71 | 73 | 91 | 93 |
| Pelleting activity recovery after 95° C. for 30 s (%) | 15 | 34 | 42 | 60 | 71 | 91 |
| Exemplifies present concept | No | No | No | No | Yes | Yes |

The granules produced using roll compaction show the highest macropore porosity and the least steam stability. Only the granules produced using spray granulation exhibit phytase (as before), which was then spray-granulated in a continuous fluidized-bed using a Glatt ProCell 5 Lab System unit. The parameters of spray granulation were adjusted such that the residence time of the cores in the ProCell unit was longer for those used to produce Granule H in comparison to those used to produce Granule G. The cores were subsequently coated in a batch fluid bed on a Vector VFC-LAB 1 unit using coating parameters in the ranges described in Example 2. The resulting granules exhibited phytase activity in the range of 90,000-100,000 FTU/g.

TABLE 2

Physical properties and steaming performance for coated phytase granules G and H

|  | Granule G | Granule H |
|---|---|---|
| Core production method | Spray granulation | Spray granulation |
| Total fermentation solids (% wt/wt) | 45 | 43 |
| Enzyme solids (% wt/wt) | 18 | 18 |
| Core sphericity | 0.8 | 0.9 |
| Core roundness | 0.2 | 0.5 |
| Coated granule macropore porosity for 0.2-8.0 µm macropores (cc/g) | 0.049 | 0.014 |
| Lab-scale steaming activity recovery after 12 s (%) | 82 | 95 |
| Pelleting activity recovery after 95° C., 30 s (%) | 32 | 75 |
| Exemplifies present concept | No | Yes |

As a result of its shorter residence time in the ProCell spray-granulation unit, the enzyme core that was used to produce Granule G showed a lower sphericity and roundness than the core that was used to produce Granule H. A longer residence time in the unit allows additional attrition and smoothing of the enzyme matrix cores. Although the macropore porosity of the cores used to produce Granule G was relatively low, the poor sphericity of the granule did not allow the deposition of an even, nonporous coating during the spray coating. The coating of finished Granule G therefore had a significantly higher macropore porosity than did the coating of finished Granule H. The steam stability of Granule G was correspondingly poorer than that of Granule H, as measured by both the laboratory scale steam test and in the pellet mill test, both described previously.

Example 4. Increasing Coating Thickness on a Spray-Granulated Core

It is noteworthy that after a sufficiently low-porosity coating has been deposited on a core, additional coating of the granules and reduction of the payload may not further improve the steaming stability. Table 3, below, summarizes physical properties and steaming performance for two coated phytase granules, designated granules J-1 and J-2. Granules J-1 and J-2 were both made from an identical set of cores produced from a UFC containing phytase (as before), which was then spray-granulated in a continuous fluidized-bed using a Glatt ProCell 5 Lab System unit.

The cores were subsequently coated in a batch fluid bed on a Vector VFC-LAB 1 unit using coating parameters in the ranges described in Example 2. The coating of each granule included a salt layer (sodium sulfate) and a hydrophobic layer (PVA/talc) that together comprised between 55-77% wt/wt of the granule. The batch size for each granule was about 1-2 kg. The resulting granules exhibited phytase activity in the range of 40,000-110,000 FTU/g.

TABLE 3

Physical properties and steaming performance for coated phytase granules J-1 and J-2

|  | Granule J-1 | Granule J-2 |
|---|---|---|
| Granule core fraction (% wt/wt) | 45 | 22 |
| Granule salt coating fraction (% wt/wt) | 43 | 62 |
| Granule hydrophobic coating fraction (% wt/wt) | 11 | 16 |
| Total fermentation solids (% wt/wt) | 45 | 22 |
| Enzyme solids (% wt/wt) | 18 | 9 |
| Granule phytase activity (FTU/g) | 110,000 | 44,000 |
| Granule $D_{50}$ (µm) | 270 | 320 |
| Enzyme core macropore porosity for 0.2-8.0 µm macropores (cc/g) | 0.029 | 0.029 |
| Coated granule macropore porosity for 0.2-8.0 µm macropores (cc/g) | 0.032 | 0.032 |
| Lab-scale steaming activity recovery after 12 s, (%) | 74 | 82 |
| Pelleting activity recovery after 95° C., 30 s, (%) | 74 | 67 |
| Exemplifies present concept | Yes | No |

Although the payload of granule J-1 is more than twice that of granule J-2, and the particle diameter is 16% smaller, the macropore porosity of the two coated granules is almost identical. Correspondingly, the overall steam stability of the two granules, as measured by both a laboratory-scale steaming test and pellet mill testing, described previously, is also similar and within the variability range of these assays. The additional coating applied to granule J-2, which was approximately 25% of the granule mass, does not further increase the steam stability of the granule. These data suggest that a well-applied, lower-porosity coating can confer identical steam stability compared to a thicker coating and reduced payload, emphasizing the importance of porosity as a performance parameter.

Example 5. Properties of Coatings Applied Under Different Coating Conditions

Four phytase granules with enzyme matrix cores coated using two different methods were prepared. Enzyme Matrix Core N is a representative sample from a set of enzyme matrix cores that were spray-granulated in a continuous fluidized-bed using a Glatt ProCell 25 Pilot System unit using a UFC containing phytase (as before). Granules P, Q, R, and S were produced from a set of cores produced in the same experimental run and all showing similar porosity results to Enzyme Matrix Core N.

Granules P and Q were produced by coating this set of spray-granulated cores on a Vector VFC-LAB 1 unit using coating parameters in the ranges described in Example 2. The batch size was about 2 kg, allowing for careful control of parameters such as humidity, fluidization, and mechanical impact stress during production. The coating conditions used were similar to those described in Example 2. Mechanical impact stress was low due to the small weight of the bed, while the spray parameters within the bed were controlled to minimize moisture content and produce granules that were as dry as possible without spray-drying the coating solids.

Granules R and S were produced by coating cores from the same set of spray-granulated cores on a larger-scale fluidized-bed coater in a batch size of about 100 kg. The larger bed weight introduced correspondingly higher mechanical stresses and allowed less fine control of all run parameters throughout the larger bed. The spray solution concentrations and spray temperatures were within the ranges described in Example 2. The fluidization air was varied between 800-1100 cubic meters per hour, depending on the mass of the bed during production. The salt solutions were sprayed at a rate between 36-60 liters per hour, and the hydrophobic coating solutions were sprayed at a rate between 20-45 liters per hour. The resulting Granules P, Q, R, and S exhibited phytase activity in the range of 75,000-95,000 FTU/g.

Table 4, below, illustrates the physical properties and steam stability of four phytase granules, with the enzyme matrix cores coated using two different methods (HG means homogeneous).

TABLE 4

Properties of phytase Granules N, P, Q, R and S

| | Enzyme Matrix Core N | Granule P | Granule Q | Granule R | Granule S |
|---|---|---|---|---|---|
| Core production method | Spray granul. | Spray granul. | Spray granul. | Spray granul. | Spray granul. |
| Granule core fraction (% wt/wt) | | 40 | 40 | 40 | 40 |
| Granule salt coating fraction (% wt/wt) | | 49 | 49 | 49 | 49 |
| Granule hydrophobic coating fraction (% wt/wt) | | 11 | 11 | 11 | 11 |
| Total fermentation solids (% wt/wt) | | 35 | 35 | 35 | 35 |
| Enzyme solids (% wt/wt) | | 15 | 15 | 15 | 15 |
| Granule $D_{50}$ (µm) | 250 | 300 | 290 | 290 | 320 |
| Macropore porosity for 0.2-8.0 µm macropores (cc/g) | 0.028 | 0.018 | 0.008 | 0.060 | 0.025 |
| Lab-scale steaming activity recovery after 12 s, (%) | | 81 | 86 | 76 | 94 |
| Pelleting activity recovery after 95° C., 30 s, (%) | | 80 | 92 | 61 | 82 |
| Batch size (kg) | | 2 | 2 | 80 | 80 |
| Mechanical stress during coating | | Low | Low | High | Moderate |
| Moisture level during coating | | Low | Low | High | Low |
| Drying time after salt layer deposition | | 10 min | 10 min | 5 min | 15 min |
| Coating appearance (via SEM) | | Smooth, HG | Smooth, HG | Broken, porous | Smooth, HG |
| Exemplifies present concept | N/A | Yes | Yes | No | Yes |

Attributable to the highest level of control over the coating properties, granules P and Q show the lowest macropore porosity, and correspondingly high steaming stability. Granule R, produced at a larger scale and under the least controlled conditions, shows a higher macropore porosity than Granules P and Q and a significantly lower steam stability in both the laboratory scale and pelleting application tests, described previously. This result is despite applying the same coating configuration of excipients to the same set of cores, and having approximately the same final diameter. The higher macropore porosity of Granule R makes clear that coating quality is poorer, and the steam stability of the granule is correspondingly lower.

Granule S was also produced on the larger-scale fluidized-bed coater in a 100 kg batch size; however, additional care was taken to reduce the mechanical impact stress during the coating process by reducing the fluidization level. The moisture content of the granule during the coating process was reduced by increasing the temperature of the salt spray from 45° C. to 50° C., spraying the salt at a slower rate, lengthening the drying times between coatings, and adding in additional drying steps. Reducing the mechanical stress and increasing the level of moisture control helped improve the homogeneity and quality of the coating throughout the entire coating process. Granule S correspondingly showed a lower macropore porosity and an improved level of steam stability when compared to Granule R, closer to the properties of Granules P and Q. These data suggest that producing a high-quality core and selecting an appropriate level of excipient coating is not sufficient to produce a successful granule; rather, the coating conditions must be carefully controlled to achieve a coating with a low macropore porosity.

Example 6. Properties of Coatings with Different Hygroscopicity

In addition to depositing a low-porosity coating, it is also necessary to deposit a coating with a low hygroscopicity. Table 5 below illustrate the physical and water uptake properties for three phytase granules, coated using different coating chemistries. Enzyme matrix cores were produced by spray granulation in a continuous fluidized-bed using a Glatt ProCell 5 Pilot System unit using a UFC containing phytase (as before). The cores were then spray-coated using a Vector VFC-LAB 1 unit with a batch size of about 2 kg. The cores were coated using different chemistries, with the coatings of granules T and U containing the hygroscopic compound maltodextrin, and the coating of granule V containing no maltodextrin. The coating parameters were within the ranges described in Example 2. For Granules T and U, rather than spraying a solution of sodium sulfate alone to deposit the salt layer, an aqueous solution containing 22.5% wt/wt sodium sulfate and 2.5% wt/wt maltodextrin was used. As a result of the different coating chemistries in their salt layers, different levels of hygroscopicity were achieved for the finished granules. The sphericity and roundness of the cores was measured using a Retsch Camsizer XT instrument and its included image processing software, analyzing at least 10,000 individual particles for each sample.

TABLE 5

Properties of phytase Granules T, U and V

| | Granule T | Granule U | Granule V |
|---|---|---|---|
| Core production method | Spray granulation | Spray granulation | Spray granulation |
| Core sphericity | 0.9 | 0.9 | 1.0 |
| Core roundness | 0.5 | 0.6 | 0.8 |
| Coated granule sphericity | 0.9 | 0.9 | 0.9 |
| Coated granule roundness | 0.6 | 0.7 | 0.9 |
| Coated granule macropore porosity for 0.2-8.0 μm macropores (cc/g) | 0.016 | 0.003 | 0.014 |
| Water uptake at 43% RH (% wt/wt) | 0.4 | 0.2 | 0.1 |
| Water uptake at 63% RH (% wt/wt) | 1.2 | 0.7 | 0.5 |
| Lab-scale steaming activity recovery after 12 s, (%) | 55 | 89 | 103 |
| Pelleting activity recovery after 95° C., 30 s, (%) | 17 | 67 | 95 |
| Total fermentation solids (% wt/wt) | 45 | 37 | 43 |
| Enzyme solids (% wt/wt) | 18 | 15 | 18 |
| Maltodextrin in final granule (% wt/wt) | 5 | 3 | 0 |
| Exemplifies present concept | No | No | Yes |

FIG. 1 illustrates the water uptake properties of the three granules, measured by dynamic vapor sorption in an AquaLab VSA system. The data shown were collected in Dynamic Vapor Sorption (DVS) mode at 25° C. and represent equilibrium measurements using an equilibrium threshold of two successive mass change events of magnitude less than 0.01%. The rates of water uptake correlate with the quantity of maltodextrin in each granule. Clearly, Granule T shows the most rapid water uptake, while granule V shows the slowest water uptake. Correspondingly, Granule V shows the highest steam stability as measured at both the laboratory and pelleting scale, while granule T shows a significantly lower steam stability. The steam stability of Granule U, which shows an intermediate level of water uptake, is marginal. This is despite all the granules showing what would otherwise be an acceptable macropore porosity. Thus, it is not sufficient to deposit a low-porosity coating; the excipients and chemistry of the coating must also be chosen to minimize the water uptake in order to ensure stability in high-moisture conditions.

Example 7: Macropore Size and Steaming Stability

For all samples exemplified above, mercury porosimetry measurements were obtained in the size range of mesopores 0.01 μm in diameter to macropores 40 μm in diameter. Within this range, the total volume of macropores within the size range of 0.2-8.0 μm in diameter shows the best correlation with steaming stability. An upper bound of 8 μm was set on this pore size range of interest, as measurement of macropores larger than 8 μm is confounded by the detection of interstices between individual granules, which can be as small as about 10 μm for granules 100-400 μm in size.

Table 6 below shows the porosity in various pore size ranges for four previously exemplified Granules C, G, P, and S. The production conditions for these granules have been described in previous examples.

TABLE 6

Properties of phytase granules C, P, G and S.

| | Granule C | Granule G | Granule P | Granule S |
|---|---|---|---|---|
| Core production method | Spray agglom. | Spray granulation | Spray granulation | Spray granulation |
| Granule enzyme fraction (% wt/wt) | 40 | 45 | 40 | 40 |
| Granule salt coating fraction (% wt/wt) | 49 | 44 | 49 | 49 |
| Granule hydrophobic coating fraction (% wt/wt) | 11 | 11 | 11 | 11 |
| Total fermentation solids (% wt/wt) | 36 | 45 | 35 | 35 |
| Enzyme solids (% wt/wt) | 14 | 18 | 15 | 15 |
| Batch size (kg) | 2 | 2 | 2 | 80 |
| Coated granule macropore porosity for 0.2-8.0 μm macropores, (cc/g) | 0.074 | 0.049 | 0.018 | 0.025 |
| Coated granule porosity for 0.01-0.2 μm pores, (cc/g) | 0.010 | 0.011 | 0.038 | 0.029 |
| Coated granule porosity for 0.01-8 μm pores, (cc/g) | 0.085 | 0.060 | 0.056 | 0.054 |
| Lab-scale steaming activity recovery after 12 s, (%) | 71 | 82 | 81 | 94 |
| Pelleting activity recovery after 95° C., 30 s, (%) | 42 | 32 | 80 | 82 |
| Exemplifies present concept | No | No | Yes | Yes |

Granules C and G exhibit a high macropore volume within the macropore size range of 0.2-8.0 μm, but a low pore volume within the pore size range of 0.01-0.2 μm. These granules show poor steam stability results, in particular extremely poor results when pelleted with animal feed. In comparison to Granules C and G, Granules P and S have a lower pore volume within the pore size range of 0.2-8.0 μm and a higher pore volume within the pore size range of 0.01-0.2 μm. These granules show much improved steam stability in comparison to Granules C and G. These data illustrate that the pore size range of 0.2-8.0 μm best correlates with the steam stability of the finished granules. The summed pore volume over the complete pore size range of 0.01-8.0 μm also does not correlate at all with steam stability.

What is claimed is:
1. An enzyme-containing coated granule comprising:
   (a) a payload of at least 10% wt/wt enzyme solids;
   (b) a continuous protective coating surrounding an enzyme matrix core resulting in a coated granule having
      (i) a porosity of less than about 0.03 cc/g for macropores within the range of 0.2-8.0 microns in diameter; and
      (ii) a water uptake of no more than 0.5% w/w water at 60% relative humidity.
2. The coated granule of claim 1, having an enzyme matrix core with a sphericity of at least 0.9.

3. The coated granule of claim 1, having an enzyme matrix core with a roundness of at least 0.5.

4. The coated granule of claim 1, having a coating mass fraction of at least 30% w/w.

5. The coated granule of claim 1, having a coating mass fraction of less than 70% w/w.

6. The coated granule of claim 1, wherein the water activity of the core is less than 0.2.

7. The coated granule of claim 1, wherein the critical relative humidity of the coating is greater than 60%.

8. The coated granule of claim 1, wherein the coating comprises non-hygroscopic materials and has a water uptake of no more than 0.5% w/w water at 60% relative humidity.

9. The coated granule of claim 1, having a coating comprising no more than 60% salt (w/w).

10. The coated granule of claim 1, having a coating comprising no less than 30% salt (w/w).

11. The coated granule of claim 1, wherein the core comprises less than 20% excipients (w/w).

12. The coated granule of claim 1, having an overall diameter of greater than 100 μm.

13. The coated granule of claim 1, having an overall diameter of less than 400 μm.

14. The coated granule of claim 1, wherein the enzyme matrix core is made by spray granulation.

15. The coated granules of claim 1, wherein the enzyme solids comprise a phytase.

16. A method for increasing the stability of an enzyme in a composition, the method comprising providing the enzyme in coated granule comprising:
 (a) a payload of at least 10% wt/wt enzyme solids;
 (b) a continuous protective coating surrounding an enzyme matrix core resulting in a coated granule having
  (i) a porosity of less than about 0.03 cc/g for macropores within the range of 0.2-8.0 microns in diameter; and
  (ii) a water uptake of no more than 0.5% w/w water at 60% relative humidity.

17. The method of claim 16, wherein the enzyme matrix core has a sphericity of at least 0.9.

18. The method of claim 16, wherein the enzyme matrix core has a roundness of at least 0.5.

19. The method of claim 16, wherein the granules have a coating mass fraction of at least 30% w/w.

20. The method of claim 16, wherein the granules have a coating mass fraction of less than 70% w/w.

21. The method of claim 16, wherein the water activity of the enzyme matrix core is less than 0.2.

22. The method of claim 16, wherein the critical relative humidity of the coating is greater than 60%.

23. The method of claim 16, wherein the coating comprises non-hygroscopic materials and has a water uptake of no more than 0.5% w/w water at 60% relative humidity.

24. The method of claim 16, wherein the coating comprises no more than 70% salt (w/w).

25. The method of claim 16, wherein the coating comprises no less than 30% salt (w/w).

26. The method of claim 16, wherein the core comprises no more than 20% excipients (w/w).

27. The method of claim 16, wherein the granule has an overall diameter of greater than 100 μm.

28. The method of claim 16, wherein the granules has an overall diameter of less than 400 μm.

29. The method of claim 16, wherein the enzyme matrix cores are made by spray granulation.

30. The method of claim 16, wherein the granule is made by spray granulation.

31. The method of claim 16, wherein the granule has a water soluble or dispersible coating comprising a wax or a hydratable salt.

32. The method of claim 16, wherein the enzyme solids comprise a phytase.

33. A pelleted animal feed composition comprising the granule of claim 1.

34. A method for increasing activity recovery of enzyme in a steam pelleting process, the method comprising providing the enzyme in coated granule comprising:
 (a) a payload of at least 10% wt/wt enzyme solids;
 (b) a continuous protective coating surrounding an enzyme matrix core resulting in a coated granule having
  (i) a porosity of less than about 0.03 cc/g for macropores within the range of 0.2-8.0 microns in diameter; and
  (ii) a water uptake of no more than 0.5% w/w water at 60% relative humidity.

35. The method of claim 34, wherein the enzyme matrix core has a sphericity of at least 0.9.

36. The method of claim 34, wherein the enzyme matrix core has a roundness of at least 0.5.

37. The method of claim 34, wherein the granules have a coating mass fraction of at least 30% w/w.

38. The method of claim 34, wherein the granules have a coating mass fraction of less than 70% w/w.

39. The method of claim 34, wherein the water activity of the enzyme matrix core is less than 0.2.

40. The method of claim 34, wherein the critical relative humidity of the coating is greater than 60%.

41. The method of claim 34, wherein the coating comprises non-hygroscopic materials and has a water uptake of no more than 0.5% w/w water at 60% relative humidity.

42. The method of claim 34, wherein the coating comprises no more than 70% salt (w/w).

43. The method of claim 34, wherein the coating comprises no less than 30% salt (w/w).

44. The method of claim 34, wherein the core comprises no more than 20% excipients (w/w).

45. The method of claim 34, wherein the granule has an overall diameter of greater than 100 μm.

46. The method of claim 34, wherein the granules has an overall diameter of less than 400 μm.

47. The method of claim 34, wherein the enzyme matrix cores are made by spray granulation.

48. The method of claim 34, wherein the granule is made by spray granulation.

49. The method of claim 34, wherein the granule has a water soluble or dispersible coating comprising a wax or a hydratable salt.

50. The method of claim 34, wherein the enzyme solids comprise a phytase.

* * * * *